United States Patent [19]

Ishizumi et al.

[11] 4,044,003
[45] Aug. 23, 1977

[54] PROCESS FOR PREPARING 1,4-BENZODIAZEPINES

[75] Inventors: Kikuo Ishizumi, Ikeda; Kazuo Mori, Kobe; Tadashi Okamoto, Ashiya; Takeshi Akase, Nishinomiya; Takahiro Izumi, Takarazuka; Mitsuhiro Akatsu, Toyonaka; Yoshiharu Kume; Shigeho Inaba, both of Takarazuka; Hisao Yamamoto, Nishinomiya, all of Japan

[73] Assignee: Sumitomo Chemical Company, Limited, Osaka, Japan

[21] Appl. No.: 598,621

[22] Filed: July 24, 1975

Related U.S. Application Data

[63] Continuation of Ser. No. 223,303, Feb. 3, 1972, abandoned.

[30] Foreign Application Priority Data

Feb. 9, 1971    Japan .................................. 46-5511
Apr. 6, 1971    Japan .................................. 46-21523
May 28, 1971    Japan .................................. 46-37196

[51] Int. Cl.² .......................................... C07D 243/16
[52] U.S. Cl. ...................... 260/239 BD; 260/239.3 D
[58] Field of Search ................................ 260/239 BD

[56] References Cited

U.S. PATENT DOCUMENTS 3,144,439   8/1964   Reeder et al. ............... 260/239 BD

OTHER PUBLICATIONS

Archer et al., Chem. Reviews, vol. 68, p. 766, (1968).
Feuer et al., J. Org. Chem., vol. 30, pp. 2877–2880, (1965).
Brown et al., J. Am. Chem. Soc., vol. 86, pp. 3566–3567, (1964).
Ishizumi et al., J. Org. Chem., vol. 37, pp. 4111–4113, (1972).

*Primary Examiner*—Raymond V. Rush
*Attorney, Agent, or Firm*—Stevens, Davis, Miller & Mosher

[57] ABSTRACT

1,4-Benzodiazepine derivatives of the formula,

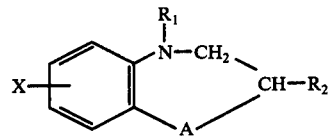

wherein $R_1$ is hydrogen, a lower alkyl, a haloalkyl, a cycloalkylalkyl, an alkoxyalkyl, an acyloxyalkyl, an alkylthioalkyl, an alkylaminoalkyl, a dialkylaminoalkyl, a hydroxyalkyl, carbamoyl, or an N-alkylcarbamoyl; $R_2$ is hydrogen or a lower alkyl; X is hydrogen, a halogen, nitro, or trifluoromethyl; A is a group of the formula,

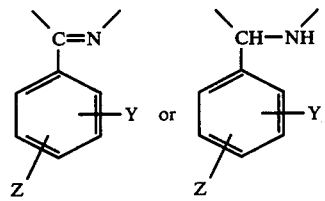

(wherein Y and Z each represent hydrogen, a halogen, a lower alkyl, or nitro) and a salt thereof, are prepared by reacting a 1,4-benzodiazepin-2-one compound of the formula,

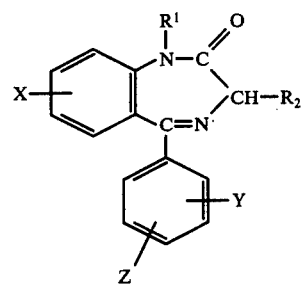

wherein $R_1$, $R_2$, X, Y and Z are the same as defined above, with diborane in an inert solvent.

8 Claims, No Drawings

PROCESS FOR PREPARING 1,4-BENZODIAZEPINES

This is a continuation of application Ser. No. 223,303 filed Feb. 3, 1972, now abandoned.

This invention relates to a novel process for preparing 1,4-benzodiazepine derivatives and salts thereof.

More particularly, this invention relates to a process for preparing 2,3-dihydro-1H-1,4-benzodiazepine derivatives and 2,3,4,5-tetrahydro-1H-1,4-benzodiazepine derivatives represented by the formula,

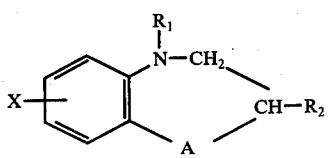

wherein $R_1$ is hydrogen, a lower alkyl, a haloalkyl, a cycloalkylalkyl, an alkoxyalkyl, an acyloxyalkyl, an alkylthioalkyl, an alkylaminoalkyl, a dialkylaminoalkyl, a hydroxyalkyl, carbamoyl, or an N-alkylcarbamoyl; $R_2$ is hydrogen or a lower alkyl; X is hydrogen, a halogen, nitro, a trifluoromethyl; A is a group of the formula,

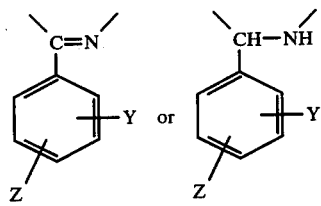

(wherein Y and Z each represent hydrogen, a halogen, a lower alkyl, or nitro) and a salt thereof.

The 1,4-benzodiazepine derivatives represented by the formula (I) have prominent effects as sedatives, anticonvulsants, and muscle relaxants, and are useful as pharmaceuticals. This invention is to provide an industrially advantageous process for preparing such therapeutically valuable compounds.

According to a known process for preparing 1,4-benzodiazepine derivatives represented by the above-mentioned formula (I), as described in Journal of Organic Chemistry, Vol. 28, p. 2456 (1963), 1,4-benzodiazepin-2-one derivatives represented by the formula,

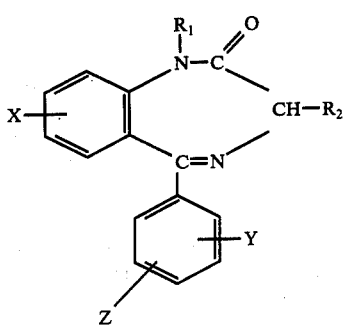

wherein $R_1$, $R_2$, X, Y and Z have the same meanings as defined above, are reduced with lithium aluminum tetrahydride. However, when this known process described in the literature is applied to the case where $R_1$ attached to the nitrogen atom at 1-position in the above-mentioned formula (II) is a substituent such as methyl group, there is obtained in a low yield of 20% solely a tetrahydro derivative which is formed as a result of additional reduction of the double bond of the grouping

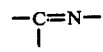

at 4 and 5 positions; it is not practically possible to obtain a 2,3-dihydro-1,4-benzodiazepine derivative (for example, 1-methyl-2,3-dihydro-5-phenyl-7-chloro-1H-1,4-benzodiazepine) which can be prepared by the process of this invention as a preferred embodiment thereof.

Further, according to recent publications (for example, German Offenlegungsschrift No. 1,958,742), it was found that in the case of reducing at a low temperature a compound, in which $R_1$ attached to a nitrogen atom at 1-position is methyl group, with lithium aluminum tetrahydride, the double bond in the grouping

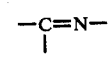

at 4- and 5-positions is not reduced, while the carbonyl group ($>C = O$) at 2-position is reduced only to the hydroxyl group

The resulting compound did not give the aimed 2,3-dihydro-1,4-benzodiazepine derivative (for example, 1-methyl-2,3-dihydro-5-phenyl-7-chloro-1H-1,4-benzodiazepine) when the reaction temperature is further raised, but unknown products.

Further, when at least one of the substituents, X, Y and Z, in the above-mentioned formula (II) is nitro group, neither corresponding 2,3-dihydro-1,4-benzodiazepine derivative nor corresponding 2,3,4,5-tetrahydro-1,4-benzodiazepine derivative can be obtained, because the said nitro group is reduced by lithium aluminum tetrahydride.

As a result of extensive researches to improve the above-said disadvantages of the conventional processes, the present inventors have found out a process for preparing in high yields 1,4-benzodiazepine derivatives represented by the aforementioned formula (I) by reducing benzodiazepin-2-one derivatives represented by the aforementioned formula (II) with diborane.

According to the process of this invention, even when at least one of the substituents, X, Y and Z, in the formula (II) contained nitro group, a corresponding 1,4-benzodiazepine derivative can be obtained in high yield and in high purity; also, even when the substituent $R_1$ at 1-position in the formula (II) is a methyl group, etc., it is possible by low temperature reduction to obtain selectively a 2,3-dihydro-1,4-benzodiazepine derivative without reducing the double bond in the grouping

at 4- and 5-positions. Consequently, the process of this invention is an extremely advantageous process in commercial operation.

According to the process of this invention, 1,4-benzodiazepine derivatives represented by the aforementioned formula (I) are obtained by treating corresponding benzodiazepin-2-one derivatives represented by the aforementioned formula (II) with diborane in an appropriate solvent.

Diborane used in the reaction according to the process of this invention can be added to the reaction mixture, or, alternatively, can conveniently formed continuously in the reaction mixture.

The solvent for use is suitably selected from inert solvents which do not interfere with the reaction, such as ether, diethylene glycol dimethyl ether, tetrahydrofuran, and the like.

The reaction of the present process proceeds with cooling, though can be conducted, if necessary, with mild heating. Application of heat generally promotes formation of the 2,3,4,5-tetrahydro derivatives of the general formula (I).

The 2,3-dihydro-1H-1,4-benzodiazepine and 2,3,4,5-tetrahydro-1H-1,4-benzodiazepine derivatives obtained by the above-mentioned process can be isolated as acid addition salts by treating with inorganic or organic acids such as hydrochloric acid, sulfuric acid, phosphoric acid, succinic acid, acetic acid, maleic acid, fumaric acid, tartaric acid, and the like.

By the process of this invention, may be prepared, for example, the following 1,4-benzodiazepine derivatives.

5-Phenyl-7-chloro-2,3-dihydro-1H-1,4-benzodiazepine

1-Methyl-5-phenyl-7-chloro-2,3-dihydro-1H-1,4-benzodiazepine

1-Ethyl-5-phenyl-7-chloro-2,3-dihydro-1H-1,4-benzodiazepine

1-Cyclopropylmethyl-5-phenyl-7-chloro-2,3-dihydro-1H-1,4-benzodiazepine

1-Methyl-7-nitro-5-phenyl-2,3-dihydro-1H-1,4-benzodiazepine

1-Methyl-5-(o-chlorophenyl)-7-chloro-2,3-dihydro-1H-1,4-benzodiazepine

1-Methyl-5-(o-fluorophenyl)-7-chloro-2,3-dihydro-1H- 1,4-benzodiazepine 5-(o-Tolyl)-7-nitro-2,3-dihydro-1H-1,4-benzodiazepine 5-Phenyl-7-trifluoromethyl-2,3-dihydro-1H-1,4-benzodiazepine 1-Methyl-5-(2',6'-difluorophenyl)-7-chloro-2,3-dihydro-1H-1,4-benzodiazepine 1-(β-Diethylaminoethyl)-5-phenyl-7-chloro-2,3-dihydro-1H-1,4-benzodiazepine 1-(β-Methylaminopropyl)-5-phenyl-2,3-dihydro-1H-1,4-benzodiazepine 1-(β-Methoxyethyl)-5-phenyl-7-chloro-2,3-dihydro-1H-1,4-benzodiazepine 1-(β-Ethoxyethyl)-5-phenyl-7-chloro-2,3-dihydro-1H-1,4-benzodiazepine 1-(β-Methoxypropyl)-5-(o-fluorophenyl)-2,3-dihydro-1H-1,4-benzodiazepine 1-(β-Bromoethyl)-5-phenyl-7-chloro-2,3-dihydro-1H-1,4-benzodiazepine 1-(β-Acetoxyethyl)-5-phenyl-7-chloro-2,3-dihydro-1H-1,4-benzodiazepine 1-(β-Ethylthioethyl)-5-(p-chlorophenyl)-6-chloro-2,3-dihydro-1H-1,4-benzodiazepine 1-(β-Ethylthiopropyl)-5-phenyl-7-chloro-2,3-dihydro-1H-1,4-benzodiazepine 1-(β-Hydroxyethyl)-5-(2',4'-dichlorophenyl)-7-trifluoromethyl-2,3-dihydro-1H-1,4-benzodiazepine 1-(N,N-Dimethylcarbamoylmethyl)-5-(o-nitrophenyl)-7-bromo-2,3-dihydro-1H-1,4-benzodiazepine 1-Carbamoylethyl-3-methyl-5-phenyl-6-nitro-2,3-dihydro-1H-1,4-benzodiazepine 1-Cyclopropylmethyl-5-(o-fluorophenyl)-7-chloro-2,3-dihydro-1H-1,4-benzodiazepine 1-Cyclobutylmethyl-5-phenyl-7-nitro-2,3-dihydro-1H-1,4-benzodiazepine 5-Phenyl-7-chloro-2,3,4,5-tetrahydro-1H-1,4-benzodiazepine 1-Methyl-5-phenyl-7-chloro-2,3,4,5-tetrahydro-1H-1,4-benzodiazepine 1-Ethyl-5-phenyl-7-chloro-2,3,4,5-tetrahydro-1H-1,4-benzodiazepine 1-Cyclopropylmethyl-5-phenyl-7-chloro-2,3,4,5-tetrahydro-1H-1,4-benzodiazepine 1-Methyl-7-nitro-5-phenyl-2,3,4,5-tetrahydro-1H-1,4-benzodiazepine 1-Methyl-5-(o-chlorophenyl)-7-chloro-2,3,4,5-tetrahydro-1H-1,4-benzodiazepine 1-Methyl-5-(o-fluorophenyl)-7-chloro-2,3,4,5-tetrahydro-1H-1,4-benzodiazepine 5-(o-Tolyl)-7-nitro-2,3,4,5-tetrahydro-1H-1,4-benzodiazepine 5-Phenyl-7-trifluoromethyl-2,3,4,5-tetrahydro-1H-1,4-benzodiazepine 1-Methyl5-(2',6'-difluorophenyl)-7-chloro-2,3,4,5-tetrahydro-1H-1,4-benzodiazepine 1-(β-Diethylaminoethyl)-5-phenyl-7-chloro-2,3,4,5-tetrahydro-1H-1,4-benzodiazepine 1-(β-Methylaminopropyl)-5-phenyl-2,3,4,5-tetrahydro-1H-1,4-benzodiazepine 1-(β-Methoxyethyl)-5-phenyl-7-chloro-2,3,4,5-tetrahydro-1H-1,4-benzodiazepine 1-(β-Ethoxyethyl)-5-phenyl-7-chloro-2,3,4,5-tetrahydro-1H-1,4-benzodiazepine 1-(β-Methoxypropyl)-5-(o-fluorophenyl)-2,3,4,5-tetrahydro-1H-1,4-benzodiazepine    1-(β-Bromoethyl)-5-phenyl-7-chloro-2,3,4,5-tetrahydro-1H-1,4-benzodiazepine 18β-Acetoxyethyl)-5-phenyl-7-chloro-2,3,4,5-tetrahydro-1H-1,4-benzodiazepine 1-(β-Ethylthioethyl)-5-(p-chlorophenyl)-6-chloro-2,3,4,5-tetrahydro-1-H-1,4-benzodiazepine 1-(β-Ethylthiopropyl)-5-phenyl-7-chloro-2,3,4,5-tetrahydro-1H-1,4-benzodiazepine 1-(β-Hydroxyethyl)-5-(2',4'-dichlorophenyl)-7-trifluoromethyl-2,3,4,5-tetrahydro-1H-1,4-benzodiazpine 1-(N,N-Dimethylcarbamoylmethyl)-5-(o-nitrophenyl-7-bromo-2,3,4,5-tetrahydro-1H-1,4-benzodiazepine 1-Carbamoylethyl-3-methyl-5-phenyl-6-nitro-2,3,4,5-tetrahydro-1H-1,4-benzodiazepine 1-Cyclopropylmethyl-5-(o-fluorophenyl)-7-chloro-2,3,4,5-tetrahydro-1H-1,4-benzodiazepine 1-Cyclobutylmethyl-5-phenyl-7-nitro-2,3,4,5-tetrahydro-1H-1,4-benzodiazepine 7-Nitro-5-phenyl-2,3,4,5-tetrahydro-1H-1,4-benzodiazepine 7-Nitro-5-phenyl-2,3-dihydro-1H-1,4-benzodiazepine 5-(o-Chlorophenyl)-7-nitro-2,3-dihydro-1H-1,4-benzodiazepine 5-(o-Fluorophenyl)-7-nitro-2,3-dihydro-1H-1,4-benzodiazepine 5-(o-Tolyl)-7-nitro-2,3-dihydro-1H-1,4-benzodiazepine 5-(p-Chlorophenyl)-6-nitro-2,3-dihydro-1H-1,4-benzodiazepine 5-(2',4'-Dichlorophenyl)-7-nitro-2,3,4,5-tetrahydro-1H-1,4-benzodiazepine 5-(o-Nitrophenyl)-7-nitro-2,3-dihyro-1H-1,4-benzodiazepine 3-Methyl-5-Phenyl-6-nitro-2,3-dihydro-1H-1,4-benzodiazepine 5-(o-Fluorophenyl)-7-nitro-2,3,4,5-tetrahydro-1H-1,4-benzodiazepine 5-(2',6'-Dichlorophenyl):7-nitro-2,3-dihydro-1H-1,4-benzodiazepine The present invention is further illustrated below with reference to Examples, which are merely illustrative and, of course, are not intended to limit the scope of the invention.

EXAMPLE 1

To a solution of 30 ml of 1.07 M diborane in tetrahydrofuran was added with stirring 1.43 g of 1-methyl-5-phenyl-7-chloro-1,3-dihydro-2H-1,4-benzodiazepin-2-one at −15° to −10° C. After further stirring at −10° C for 2 hours, the reaction mixture was poured into 100 ml of ice-water and 20 ml of concentrated hydrochloric acid was added thereto. The mixture was reflexed for one hour. After having been cooled, the resultant red solution was neutralized with 28%-aqueous ammonia, and then extracted with ether. The ether extract was washed with water and dried over anhydrous sodium sulfate, and the solvent was removed under reduced pressure. There were obtained 1.35 g of 1-methyl-5-phenyl-7-chloro-2,3-dihydro-1H-1,4-benzodiazepine, which were recrystallized from n-hexane to give prisms melting at 99.5° to 101,0° C.

EXAMPLE 2

To a suspension of 2.28 g of sodium borohydride in 35ml of tetrahydrofuran was added dropwise with stirring a solution of 13.0 g of boron trifluoride etherate in 10ml of tetrahydrofuran below 10° C, and the mixture was stirred at room temperature for 45 minutes. To the mixture was added dropwise solution of 1.43 g of 1-methyl-5-phenyl-7-chloro-1,3-dihydro-2H-1,4-benzodiazepin-2-one in 10 ml of tetrahydrofuran at −15° to −12.5° C over a period of 5 minutes, and then the mixture was stirred at =15° C for 22 hours. The reaction mixture was poured into 100 ml of ice-water, and then 20 ml of concentrated hydrochloric acid was added. The mixture was refluxed for 30 minutes, then cooled, and neutralized with concentrated ammonia. The tetrahydrofuran layer was separated, and the aqueous layer was extracted with ether. The combined organic layer was washed with water and dried over anhydrous sodium sulfate, and the solvent was removed under reduced pressure to obtain 1.4 g of 1-methyl-5-phenyl-7-chloro-2,3-dihydro-1H-1,4-benzodiazepine.

EXAMPLE 3

To a solution of 30 ml of 1.07 M diborane in tetrahydrofuran was added with stirring 1.48 g of 1-methyl-5-phenyl-7-nitro-1,3-dihydro-2H-1,4-benzodiazepin-2-one at −13° to −8° C, and the mixture was further stirred at −8° C for 1 hour and 45 minutes. The reaction mixture was poured into ice-water, and 20 ml of concentrated hydrochloric acid was added. The mixture was refluxed for one hour. After cooling, the resultant solution was neutralized with 28%-aqueous ammonia, and extracted with chloroform. The chloroform extracts were washed with water and dried over anhydrous sodium sulfate, and the solvent was removed under reduced pressure. The residue was dissolved in a 20%-solution of hydrochloric acid in ethyl alcohol, and refluxed for 10 minutes. The alcohol was removed by distillation under reduced pressure, and the residue was distributed between water and chloroform. The chloroform layer was separated, washed with water, and dried over anhydrous sodium sulfate. The solvent was removed by distillation under reduced pressure to obtain 1.34 g of 1-methyl-5-phenyl-7-nitro-2,3-dihydro-1H-1,4-benzodiazepine, which was recrystallized from isopropyl alcohol to yield yellow flakes melting at 186° to 187° C.

EXAMPLE 4

To a solution of 30 ml of 1.07 M diborane in tetrahydrofuran was added with stirring 1.36 g of 5-phenyl-7-chloro-1,3-dihydro-2H-1,4-benzodiazepin-2one at −13° to −8.5° C, and the mixture was further stirred at −8.5+ C for 2.5 hours. The mixture was treated in a manner similar to that in Example 1 to obtain 1.38 g of 5-phenyl-7-chloro-2,3-dihydro-1H-1,4,-benzodiazepine, which was recrystallized from a mixed solution of ether and n-petane to show a melting point of 172 to 174° C.

In a similar manner, the following compounds could be prepared:

5-Phenyl-7-nitro-2,3-dihydro-1H-1,4-benzodiazepine, yellow prisms after recrystallization from acetone; melting point, 211° to 212° C.

5-Phenyl-2,3-dihydro-1H-1,4-benzodiazepine, needles after recrystallization from petroleum ether; melting point, 144° to 146° C.

1-Methyl-5-phenyl-7-trifluoromethyl-2,3-dihydro-1H-1,4-benzodiazepine, pale yellow prisms after recrystallization from n-hexane; melting point, 150.5° to 152° C.

1-Methyl-5-phenyl-7-bromo-2,3-dihydro-1H-1,4-benzodiazepine, yellow prisms afer recrystallization from n-hexane; melting point 105° C.

1-Methyl-5-(o-fluorophenyl)-7-chloro-2,3-dihydro-1H-1,4-benzodiazepine hydrochloride; melting point, 246° to 247° C (decomp.) after recrystallization from methanol-acetone.

5-(o-Chlorophenyl)-7-chloro-2,3-dihydro-1H-1,4-benzodiazepine, prisms after recrystallization from benzene-petroleum ether; melting point, 174° to 176° C.

3-Methyl-5-phenyl-7-chloro-2,3-dihydro-1H-1,4-benzodiazepine, pale yellow prisms after recrystallization from ether-petroleum ether; melting point, 127° to 128° C.

1-Ethoxymethyl-5-phenyl-7-chloro-2,3-dihydro-1H-1,4-benzodiazepine citrate; melting point, 136° to 140° C after recrystallization from ethyl alcohol-ether.

1-Methylthiomethyl-5-phenyl-7-chloro-2,3-dihydro-1H-1,4-benzodiazepine maleate; melting point, 158° to 159° C after recrystallization from isopropyl alcohol.

1-Diethylaminoethyl-5-phenyl-7-chloro-2,3-dihydro-1H-1,4-benzodiazepine hydrochloride; melting point, 234° to 236° C after recrystallization from isopropyl alcohol.

5-(o-Fluorophenyl)-7-chloro-2,3-dihydro-1H-1,4-benzodiazepine; melting point, 163° to 164.5° C.

1-Methyl-5-(o-chlorophenyl)-7-chloro-2,3-dihydro-1H-1,4-benzodiazepine; melting point, 93° to 94.5° C.

1-Methyl-5-(o-fluorophenyl)-7-chloro-2,3-dihydro-1H-1,4-benzodiazepine; melting point, 91° to 92.5° C.

1-Cyclopropylmethyl-5-(o-chlorophenyl)-7-chloro-2,3-dihydro-1H-1,4-benzodiazepine; melting point, 88° to 89° C.

1-Cyclopropylmethyl-5-phenyl-7-trifluoromethyl-2,3-dihydro-1H-1,4-benzodiazepine hydrochloride; melting point, 244° to 246° C (decomp.).

1-Diethylaminoethyl-5-phenyl-7-nitro-2,3-dihydro-1H-1,4-benzodiazepine dihydrochloride; melting point, 234° to 236° C.

EXAMPLE 5

To a solution of 50 ml of 1.07 M diborane in tetrahydrofuran was added with stirring 1.43 g of 1-methyl-5-phenyl-7-chloro-1,3-dihydro-2H-1,4-benzodiazepin-2-one at room temperature, and the mixture was refluxed with stirring for 7.5 hours. After having been left standing overnight, 5 ml of water followed by 5 ml concentrated hydrochloric acid was added to decompose the excess diborane, and the mixture was refluxed for one hour. After cooling, the solution was neutralized with concentrated ammonia, and extracted with ether. The ether extract was washed with water and dried over anhydrous sodium sulfate, and the solvent was ramoved under reduced pressure. The residue was recrystallized from n-pentane to obtain 1.30 g of 1-methyl-5-phenyl-7-chloro-2,3,4,5-tetrahydro-1H-1,4-benzodiazepine, melting at 66° to 68° C.

EXAMPLE 6

To a mixture of 1.36g of 5-phenyl-7-chloro-1,3-dihydro-2H-1,4-benzodiazepin-2-one and 2.28 g of sodium borohydride in 35 ml of tetrahydrofuran was added dropwise with stirring a solution of 11.4 g of boron trifluoride etherate in 5 ml of tetrahydrofuran at a temperature of 25° C or lower.

After having been stirred for 2 hours at 25° C, the reaction mixture was refluxed for 3 hours. After cooling, 15 ml of water followed by 15 ml of concentrated hydrochloric acid was added to decompose the excess diborane. The mixture was refluxed for one hour, then cooled, and neutralized with concentrated ammonia. The tetrahydrofuran layer was separated, and the aqueous layer was extracted with ether. The organic solvent layers were combined, washed with water, dried over anhydrous sodium sulfate, and the solvent was removed by distillation under reduced pressure. The oily residue was dissolved in ethanol, and ethanolic hydrogen chloride was added thereto in excess.

To the resulting solution was added ether, and the precipitated crystals were collected by filtration to obtain 1.47 g of 5-phenyl-7-chloro-2,3,4,5-tetrahydro-1H-1,4-benzodiazepine having a melting point of 253.5° to 254° C (decomp.) after recrystallization from isopropanol.

EXAMPLE 7

To a mixture of 1.84 g of 1-methyl-5-phenyl-7-nitro-1,3,-dihydro-2H-1,4-benzodiazepin-2-one and 2.28 g of sodium borohydride in 30 ml of tetrahydrofuran was added dropwise with stirring a solution of 11.4 g of boron trifluoride etherate in 10 ml of tetrahydrofuran at a temperature up to 30° C.

After having been stirred for 3.5 hours at room temperature, the reaction mixture was refluxed for one hour. After cooling, 20 ml of water followed by 20 ml of concentrated hydrochloric acid was added to decompose the excess diborane, and the mixture was refluxed for 2 hours. After removal of the tetrahydrofuran by distillation under atmospheric pressure, the reaction mixture was cooled, neutralized with concentrated ammonia, and extracted with ether. The extract solution was washed with ether, dried over anhydrous sodium sulfate, and distilled under reduced pressure. The residue was subjected to chromatography using 40 g of silica gel. Elution with ethyl acetate gave 0.84 g of 1-methyl-5-phenyl-7-nitro-2,3,4,5-tetrahydro-1H-1,4-benzodiazepine having a melting point of 96° to 99° C after recrystallization from isopropanol. The hydrochloride obtained by treating the product with ethanolic hydrogen chloride showed a melting point of 295° to 297° C (decomp.).

EXAMPLE 8

To a mixture of 1.41 g of 5-phenyl-7-nitro-1,3-dihydro-2H-1,4-benzodiazepin-2-one and 2.28 g of sodium borohydride in 35 ml of tetrahydrofuran was added dropwise with stirring a solution of 11.4 g of boron trifluoride etherate in 5 ml of tetrahydrofuran, at a temperature up to 25° C. After having been stirred for 4 hours at room temperature, 20 ml of water followed by 20 ml of concentrated hydrochloric acid was added to decompose the excess diborane, and the mixture was refluxed for one hour.

After cooling, the mixture was neutralized with concentrated ammonia, and the tetrahydrofuran layer was separated. The aqueous layer was extracted with chloroform. The organic layers were combined, washed with water, dried over anhydrous sodium sulfate, and the solvent was removed by distillation under reduced pressure. The residue was washed with ether, and recrystallized from ethanol to obtain 1.245 g of 5-phenyl-7-nitro-2,3,4,5-tetrahydro-2H-1,4-benzodiazepine, which showed a melting point of 216° to 217° C after recrystallization from ethanol.

What is claimed is:

1. A process for producing 1-methyl-5-phenyl-7-chloro-2,3-dihydro-1H-1,4-benzodiazepine which comprises reducing 1-methyl-5-phenyl-7-chloro-1,3-dihydro-2H-1,4-benzodiazepin-2-one with diborane.

2. A process for producing 1-methyl-5-(o-fluorophenyl)-7-chloro-2,3-dihydro-1H-1,4-benzodiazepine which comprises reducing 1-methyl-5-(o-fluorophenyl)-7-chloro-1,3-dihydro-2H-1,4-benzodiazepin-2-one with diborane.

3. A process for producing 1-methyl-5-(o-chlorophenyl)-7-chloro-2,3-dihydro-1H-1,4-benzodiazepine which comprises reducing 1-methyl-5-(o-chlorophenyl)-7-chloro-1,3-dihydro-2H-1,4-benzodiazepin-2one with diborane.

4. A process for producing 1-methyl-5-phenyl-7-chloro-2,3,4,5-tetrahydro-1H-1,4-benzodiazepine which comprises reducing 1-methyl-5-phenyl-7-chloro-1,3-dihydro-2H-1,4-benzodiazepin-2-one with diborane with application of heat.

5. A process for producing 1-methyl-5-phenyl-7nitro-2,3-dihydro-1H-1,4-benzodiazepine which comprises reducing 1-methyl-5-phenyl-7-nitro-1,3-dihydro-2H-1,4-benzodiazepin-2-one with diborane.

6. A process for producing 1-methyl-5-phenyl-7-trifluoromethyl-2,3-dihydro-1H-1,4-benzodiazepine which comprises reducing 1-methyl-5-phenyl-7-trifluoromethyl-1,3-dihydro-2H-1,4-benzodiazepin-2-one with diborane.

7. A process for producing 1-methyl-5-phenyl-7-bromo-2,3-dihydro-1H-1,4-benzodiazepine which comprises reducing 1-methyl-5-phenyl-7-bromo-1,3-dihydro-2H-1,4-benzodiazepin-2one with diborane.

8. A process for producing 1-methyl-5-phenyl-7-nitro-2,3,4,5-tetrahydro-1H-1,4-benzodiazepine which comprises reducing 1-methyl-5-phenyl-7nitro-1,3-dihydro-2H-1,4-benzodiazepin-2-one with diborane with application of heat.

* * * * *